(12) United States Patent
Kim et al.

(10) Patent No.: US 8,906,391 B2
(45) Date of Patent: Dec. 9, 2014

(54) THERMOROD FOR ACTIVE DRUG RELEASE AND METHOD FOR MANUFACTURING THE SAME

(75) Inventors: Young Kon Kim, Busan (KR); Jae Geun Park, Busan (KR); Sang Guon Lee, Busan (KR); Woon Sub Baek, Busan (KR)

(73) Assignees: Korea Sangsa Co., Ltd. (KR); Young Kon Kim (KR)

( * ) Notice: Subject to any disclaimer, the term of this patent is extended or adjusted under 35 U.S.C. 154(b) by 994 days.

(21) Appl. No.: 12/908,686

(22) Filed: Oct. 20, 2010

(65) Prior Publication Data

US 2011/0034871 A1    Feb. 10, 2011

Related U.S. Application Data

(63) Continuation of application No. PCT/KR2008/006356, filed on Oct. 29, 2008.

(30) Foreign Application Priority Data

May 23, 2008  (KR) .................. 10-2008-0047988

(51) Int. Cl.
  *A61K 9/00* (2006.01)
  *A61K 9/14* (2006.01)
  *A61F 7/12* (2006.01)

(52) U.S. Cl.
  CPC ............. *A61K 9/0009* (2013.01); *A61K 9/0024* (2013.01); *A61K 9/0092* (2013.01)
  USPC ............ 424/400; 424/484; 424/486; 604/113

(58) Field of Classification Search
  CPC . A61K 9/0009; A61K 9/0024; A61K 9/0092; A61K 9/143
  USPC ............................ 424/400, 484, 486; 604/113
  See application file for complete search history.

(56) References Cited

U.S. PATENT DOCUMENTS

| 5,401,377 | A | * | 3/1995 | Shieh et al. | ............... 204/403.06 |
| 5,830,207 | A | * | 11/1998 | Leeb et al. | ................. 604/890.1 |
| 2005/0037075 | A1 | * | 2/2005 | Farokhzad et al. | ........... 424/468 |
| 2007/0218099 | A1 | | 9/2007 | Kim et al. | |
| 2007/0275066 | A1 | | 11/2007 | Cho et al. | |

FOREIGN PATENT DOCUMENTS

| KR | 10-2006-0025648 A | 3/2006 |
| WO | 2004/028503 A1 | 4/2004 |
| WO | 2005/016305 A1 | 2/2005 |

OTHER PUBLICATIONS

Hsieh et al. Proc. Natl. Acad. Sci, 981, 78(3), 1863-1867.*
International Search Report/ PCT/KR2008/006356, May 19, 2009.

* cited by examiner

*Primary Examiner* — Abigail Fisher
(74) *Attorney, Agent, or Firm* — Park & Associates IP Law, P.C.

(57) ABSTRACT

Disclosed is a thermorod capable of actively releasing drugs according to temperature of the thermorod and a method of manufacturing the same. The thermorod generates heat by eddy current loss and hysteresis loss in an induced magnetic field. The thermorods can effectively administer drugs, such as anti-cancer drugs, since the thermorods may be used to perform local hyperthermia at 36.5° C. or above and to actively control the active drug release and delivery according to temperature as well. The thermorods may be useful in the treatment of resting tumor cells along with hyperthermia by performing a surgical operation on lesion sites of biological tissues. Using the thermorod, the drug is effectively delivered to an affected part in response to the active drug release. This can minimize the toxicity caused by an increase in blood drug concentration, which occurs when a drug is administered by a conventional method.

9 Claims, 9 Drawing Sheets

THERMOROD FOR ACTIVE DRUG RELEASE AND METHOD FOR MANUFACTURING THE SAME

REFERENCE TO RELATED APPLICATIONS

This a continuation of pending International Patent Application PCT/KR2008/006356 filed on Oct. 29, 2008, which designates the United States and claims priority of Korean Patent Applications No. 10-2008-0047988 filed on May 23, 2008, the entire contents of which are incorporated herein by reference.

FIELD OF THE INVENTION

The present invention relates, in general, to a thermorod for active drug release capable of actively releasing drugs according to temperature and a method of manufacturing the same and, more particularly, to a thermorod for active drug release capable of actively releasing a constant concentration of drugs at a constant temperature by forming a mixed-drug layer or forming a mixed-drug layer and a coating layer on a surface thereof, and a method of manufacturing the same.

BACKGROUND OF THE INVENTION

Paclitaxel is generally used in cancer chemotherapy regimens to treat tumors. Chemotherapy using paclitaxel is carried out by intravenously injecting paclitaxel at a dosage of 135~175 mg/m$^2$ into the human body for 3 or more hours once every 3-week period in order to allow paclitaxel to spread throughout the entire body. In this case, paclitaxel is repeatedly administered approximately 4 to 6 times, or possibly more, creating a treatment regime lasting at least 6 months. The in vivo administered paclitaxel reaches affected parts through a complicated physiologic process before showing its medical effects.

Paclitaxel begins to exert medical effects following a gradual increase in its blood concentration which increases in stages throughout the cancer therapy process, so that when the paclitaxel blood concentration continually increases its toxicity becomes evident, and the generation of bone marrow is suppressed, resulting in a reduction in leukocytes and then in increased side effects such as hair loss, peripheral nerve disorder, muscular pain, etc.

Also, it has been reported that since most anti-cancer agents comprising paclitaxel have no effects on resting cells but a mortal one on growing cells, cancer chemotherapy is not effective in treating tumors whose cells divide very slowly, such as prostate cancer. That is to say, in the treatment of tumors whose cells are dividing too slowly, such as prostate cancer, the most serious problem is that not only are cells newly created as a result of cell division apoptotic, but also aged tumor cells do not die.

Presently, a variety of minimally invasive ablation technologies have been studied to treat prostate cancer. For example, radioactive seed implantation using a radioactive isotope includes brachytherapy in the biological tissues, high dose rate brachytherapy, cryoablation, etc.

Radioactive isotope implantation is used to treat tumors by inserting an implant manufactured with Iodine-125 or Palladium-103 into target tissues, but has a problem in that it is impossible to determine a dosage of the isotope suitable for the elimination of cancer. Iridium-192 implants are used in the case of high-dose brachytherapy, but have the restrictive difficulty in removing a radioactive implant from a catheter.

Cryoablation is a therapy including inserting a 6~8 inch-long tube in the prostate via the rectum and circulating liquid nitrogen through the tube to freeze an affected part. Cryoablation is simple and rarely has complications, but has a problem in that side effects such as urinary obstruction may result following treatment, and thus the catheter should remain inserted in the catheter for a long time. In the U.S.A., about 30% of prostate cancer patients undergo cryoablation, and 27% among them suffer from the symptoms of urinary incontinence. In order to minimize these side effects, tissues around the urethra should be troublesomely warmed to an adequate temperature during the cryotherapy procedure to protect the tissues from damage.

SUMMARY OF THE INVENTION

Accordingly, the present invention has been made keeping in mind the above problems occurring in the prior art, and an object of the present invention is to provide a thermorod for active drug release capable of actively releasing a constant concentration of drugs at a constant temperature by forming a mixed-drug layer on the surface thereof, and a method for manufacturing the same.

Another object of the present invention is to provide a thermorod for active drug release further comprising a coating layer formed on the surface of the mixed-drug layer surface in order to control the release of drugs, and a method for manufacturing the same.

In order to accomplish the above objects, the present invention provides a method for manufacturing a thermorod for active drug release that generates heat by means of eddy current loss and hysteresis loss in the induced magnetic field. Here, the method includes: processing the thermorod into a certain shape; preparing a mixed-drug specimen by mixing a drug with a high molecular compound acting as a support of the drug; and forming a mixed-drug layer on the surface of the thermorod by using the mixed-drug specimen, and a thermorod for active drug release manufactured by the method.

In this case, the thermorod may be made of at least one selected from the group consisting of iron, stainless steel, duplex stainless steel, nickel-copper alloy, iron-nickel alloy, palladium-cobalt alloy, iron-chromium alloy and iron-cobalt alloy. Also, the thermorod may be processed into one shape selected from the group consisting of linear, platy, coiled or tubular shapes.

Also, the high molecular compound may include polyethylene-co-vinyl acetate.

In addition, the method according to the one exemplary embodiment of the present invention may further include: forming a coating layer on the surface of the mixed-drug layer, the coating layer being made of a high molecular compound for the purpose of dip coating. In this case, the coating layer may be formed from a dip-coating solution prepared by dissolving polyethylene-co-vinyl acetate, poly (isobutyl-methacrylate) or a mixture thereof in tetrahydrofuran.

Here, the thermorod for active drug release may have a controlled drug release rate according to temperature.

Advantageous Effects

As described above, the method according to one exemplary embodiment of the present invention and the thermorod prepared by the method may be useful in effectively treating affected parts with drugs or anti-cancer drugs since they may be used to induce local hyperthermia at 36.5° C. or above and to actively control the release and delivery of the active drugs depending on temperature as well.

Also, the method according to one exemplary embodiment of the present invention and the thermorod prepared by the method may be useful in the treatment of resting tumor cells along with the inducement of hyperthermia by performing a surgical operation on lesion sites of biological tissues using the thermorod promoting active drug release, and may minimize the toxicity caused by an increase in concentration of the drug in the blood, which is generated when a drug is administered by a conventional method, since the drug is effectively delivered to an affected part in response to the active drug release.

BRIEF DESCRIPTION OF MAJOR PARTS IN THE DRAWINGS

10: duplex stainless steel
20: mixed-drug layer
30: coating layer

DETAILED DESCRIPTION OF THE INVENTION

Hereinafter, embodiments of the present invention will be described in detail with reference to the attached drawings.

Figure 1:
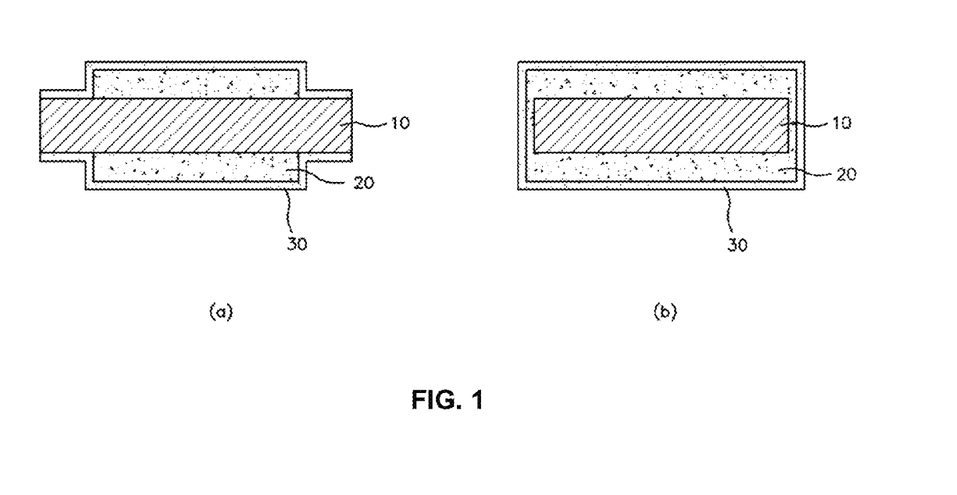
FIG. 1 is a cross-sectional view showing a thermorod for active drug release according to one exemplary embodiment of the present invention.

FIG. 1 is a cross-sectional view showing a thermorod for active drug release according to one exemplary embodiment of the present invention. Here, FIG. 1 (a) shows that a mixed-drug layer 20 and a coating layer 30 are formed only in the side surfaces of the thermorod, and FIG. 1 (b) shows that a mixed-drug layer 20 and a coating layer 30 are formed in all surfaces of the thermorod.

As shown in FIG. 1, the thermorod for active drug release according to one exemplary embodiment of the present invention is associated with a thermorod for drug release, in which heat is generated by eddy current loss and hysteresis loss especially in the induced magnetic field. In this case, only a mixed-drug layer 20 may be formed in the surfaces of the thermorod, or a mixed-drug layer 20 and a coating layer 30 may be formed together in the surfaces of the thermorod in order to control the release of drugs.

The thermorod may be made of metallic or non-metallic substances which generate heat in the induced magnetic field and control temperature, and is preferably made of one substance selected from the group consisting of iron, stainless steel, duplex stainless steel, nickel-copper alloy, iron-nickel alloy, palladium-cobalt alloy, iron-chromium alloy and iron-cobalt alloy. In particular, the duplex stainless steel (DSS) is a stainless steel having a structure in which magnetic phase ($\alpha$ phase) and non-magnetic phase ($\gamma$ phase) are mixed, and comprises iron, chromium and nickel as main components.

The thermorod may be processed into various shapes such as linear, platy, coiled or tubular shapes, depending on the purposes of treatment and its use and the site of the lesion. According to one exemplary embodiment of the present invention, duplex stainless steel is processed into a cylindrical shape of a certain diameter and length. Duplex stainless steel having a diameter of approximately 1.0 mm and a length of 10.0 mm is used herein.

The exothermic principle of the thermorod manufactured with the duplex stainless steel is that an eddy current is generated on the surface of the metallic thermorod placed inside a coil forming an induced magnetic field, Joule's heat of the eddy current generating heat. The intensity of the eddy current generated on the surface of the thermorod varies according to the magnetic properties of the thermorod and the intensity of the applied induced magnetic field.

The largest amount of heat is generated on the surface where the highest amount of eddy current is formed, and is exponentially reduced due to the generation of a counter electromotive force as the thermorod moves inside from the surface thereof. Since Joule's heat is suddenly changed in the vicinity of the Curie point where a magnetic transformation appears due to the physical change in temperature, the thermorod may maintain a constant temperature.

Also, since duplex stainless steel has a crystal structure showing magnetic properties and a crystal structure showing non-magnetic properties together, an exothermic value may be adjusted in control of magnetic ratio of the crystal structures. Therefore, it is possible to manufacture thermorods whose temperature may be maintained at a constant level by using these properties of the crystal structures.

Exothermic temperature of the thermorod may change in accordance with the chemical composition of materials, the heat-treatment conditions, the external shape, the intensity and frequency of an induced magnetic field, the intersection angles between a magnetic field and the thermorod, etc. In such cases, the active drug release in which a release rate of drugs varies in accordance with changes in temperature of the thermorod may be realized by coating the surface of the thermorod, which is able to maintain its constant temperature, with a drug and inserting the thermorod into biological tissue.

Also, when duplex stainless steel is processed into a shape with a certain diameter and length, a mixed-drug specimen having a mixed-drug layer is formed on the surface of the duplex stainless steel.

The mixed-drug specimen is prepared by mixing a drug with a high molecular weight compound acting as a support for the drug. The drug itself which is to be administered may be chosen depending on the lesions of the target patients. When an anti-cancer agent is used as the drug in the thermorod for chemotherapy, it is used in the form of Taxane-based paclitaxel or Docetaxel powder. According to one exemplary embodiment of the present invention, erythromycin and acetaminophen having hydrophobicity similar to that of the anti-cancer agent are used herein. Characteristics of these drugs are listed in the following Table 1.

TABLE 1

| Drug | Chemical formula | Tm (° C.) | M.W. (g/mol) | Hydrophobicity (Log P) |
|---|---|---|---|---|
| Acetaminophen | $C_8H_9NO_2$ | 167~172 | 151.16 | 0.917 |
| Erythromycin | $C_{37}H_{67}NO_{13}$ | 191 | 733.93 | 3.06 |

TABLE 1-continued

| Drug | Chemical formula | Tm (° C.) | M.W. (g/mol) | Hydrophobicity (Log P) |
|---|---|---|---|---|
| Paclitaxel | $C_{47}H_{51}NO_{14}$ | 213~216 | 853.9 | 5.029 |
| Docetaxel | $C_{43}H_{53}NO_{14}$ | 232 | 807.87 | 4.258 |

Also, since at a certain temperature (glass transition temperature) the high molecular weight compound used to manufacture the mixed-drug specimen is reduced in its ability to support the drugs, materials vitrified from the drug were used, and the use of bead-type polyethylene-co-vinyl acetate (hereinafter, referred to as "PEVA") which is inexpensive and stable in respect to drugs is preferable.

The PEVA was manufactured into a powdery shape using a grinder, and the acetaminophen was made into a powder at a room temperature using a grinder. Then, the drug powder and the PEVA powder with a size of 125 to 250 μm screened through ASTM Sieve No. 60 were obtained and mixed, using a mixer and vibrator, to prepare a mixed-drug specimen.

The mixed-drug specimen was used to form a mixed-drug layer on the surface of the duplex stainless steel thermorod. A suitable amount of the mixed-drug specimen powder was put into a cylindrical mold (I.D.; φ1.5 mm, O.D.; φ30 mm), and the mold was pressured at a load of 1.5 kg at a temperature of approximately 90° C. for approximately 15 minutes. After the heating and pressuring steps, a duplex stainless steel thermorod (drug Mixture thermorod, hereinafter referred to as "DMT") having a mixed-drug layer formed therein was obtained by cooling the mixed-drug specimen to room temperature to form a mixed-drug layer (thickness 0.27 mm) on the surface of the duplex stainless steel (φ1.0 mm, length 43.0 mm).

Figure 2:
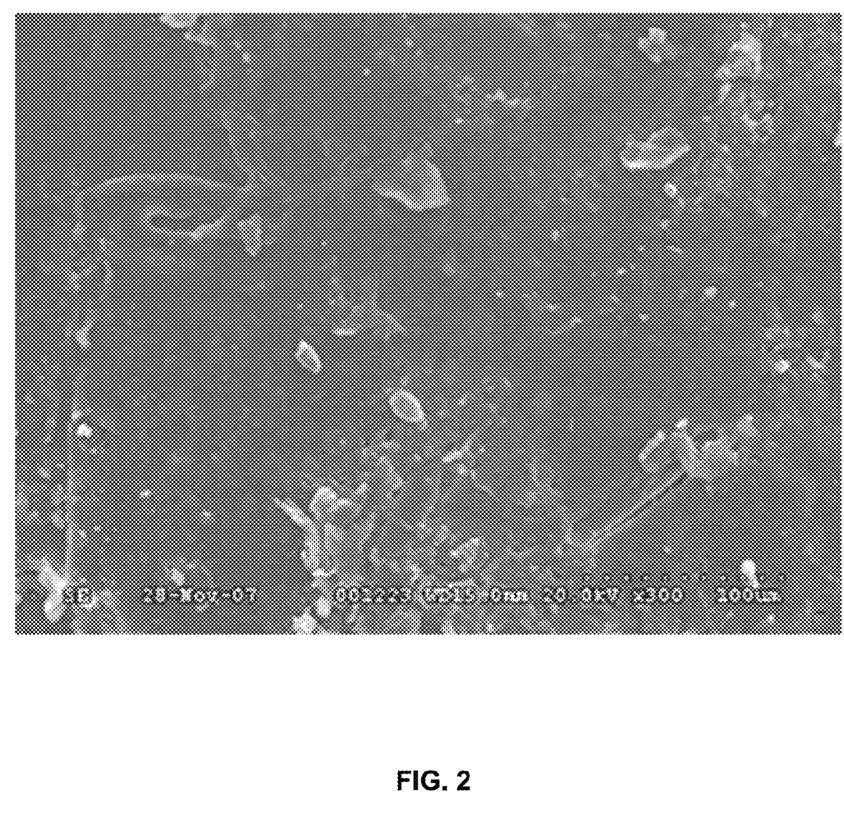
FIGS. 2 and 3 are SEM photographs showing a surface and a cross section of a duplex stainless steel thermorod having a mixed-drug layer formed therein according to one exemplary embodiment of the present invention.
Figure 3:
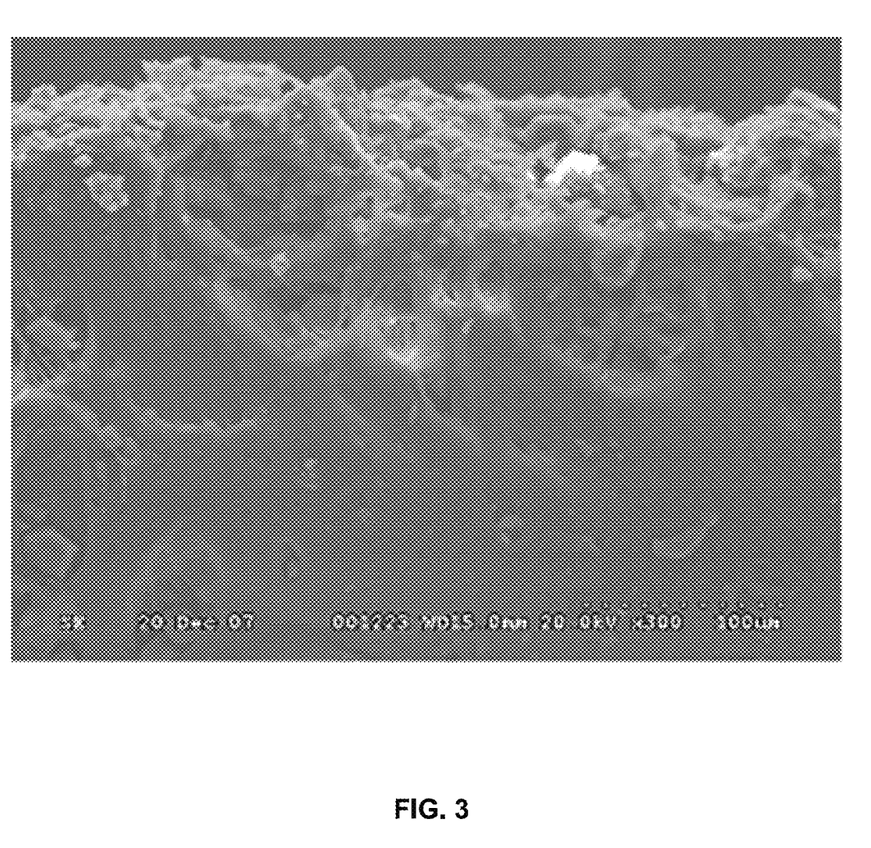

FIGS. 2 and 3 are SEM photographs showing a surface and a cross section of a duplex stainless steel thermorod having a mixed-drug layer formed therein. As shown in FIGS. 2 and 3, it is revealed that the drug particles are generally distributed within a diameter of 50 μm.

Meanwhile, a coating layer made of a high molecular weight compound may be additionally formed on the surface of the duplex stainless steel having a mixed-drug layer formed therein. The coating layer was used to suppress the release, particularly burst release of the drug from the mixed-drug layer formed in the duplex stainless steel thermorod, and the release rate of the drug may be controlled by adjusting the thickness of the coating layer, etc.

Materials vitrified at a certain temperature (glass transition temperature) were used as the high molecular weight compound which formed the coating layer, and bead-type polyethylene-co-vinyl acetate (hereinafter, referred to as "PEVA") and crystalline poly(isobutyl methacrylate) (hereinafter, referred to as "PBMA") were purchased from Aldrich and used, both of which are stable to the used temperature and to the released drugs. Tetrahydrofuran (hereinafter, referred to as 'THF') was used as an organic solvent used to dissolve a polymer to manufacture a dip-coating polymer solution. The characteristics of the high molecular weight compounds for dip coating are listed in the following Table 2.

Chemical Formula of PEVA

Chemical Formula of PBMA

TABLE 2

| Biostable Polymer | Type | $T_g$ | $T_m$ | Density (g/) |
|---|---|---|---|---|
| PEVA | Bead | 46 | 74 | 0.948 |
| PBMA | Crystalline | 55 | 86 | 1.09 |

The dip-coating polymer solution was prepared as follows. 20 ml of THF was poured into a 100 ml beaker, and its temperature was maintained at 50° C. in a water bath (Jeio tech co.). Then, PEVA/TTHF (the volume ratio of PEVA:THF was 3:97), PEVA/PBMA/THF (the volume ratio of PEVA:PBMA:THF was 2.1:0.9:97), and PEVA/PBMA/THF (the volume ratio of PEVA:PBMA:THF was 0.9:2.1:97) as the high molecular weight compounds were completely dissolved in an organic solvent to prepare 3 dip-coating polymer solutions. The duplex stainless steel having a mixed-drug layer formed therein was dipped in each of the 3 solutions for 5 seconds, and dried at room temperature for 6 hours or more to form a dip-coating layer.

Then, a thermorod dip-coated with the PEVA/THF (a volume ratio of PEVA:THF was 3:97) solution was manufactured (hereinafter, referred to as "PDMT"), a thermorod dip-coated with the PEVA/PBMA/THF (the volume ratio of PEVA:PBMA:THF was 2.1:0.9:97) solution was manufactured (hereinafter, referred to as "HPDMT"), and a thermorod dip-coated with the PEVA/PBMA/THF (the volume ratio of PEVA:PBMA:THF was 0.9:2.1:97) solution was manufactured (hereinafter, referred to as "LPDMT").

Figure 4:
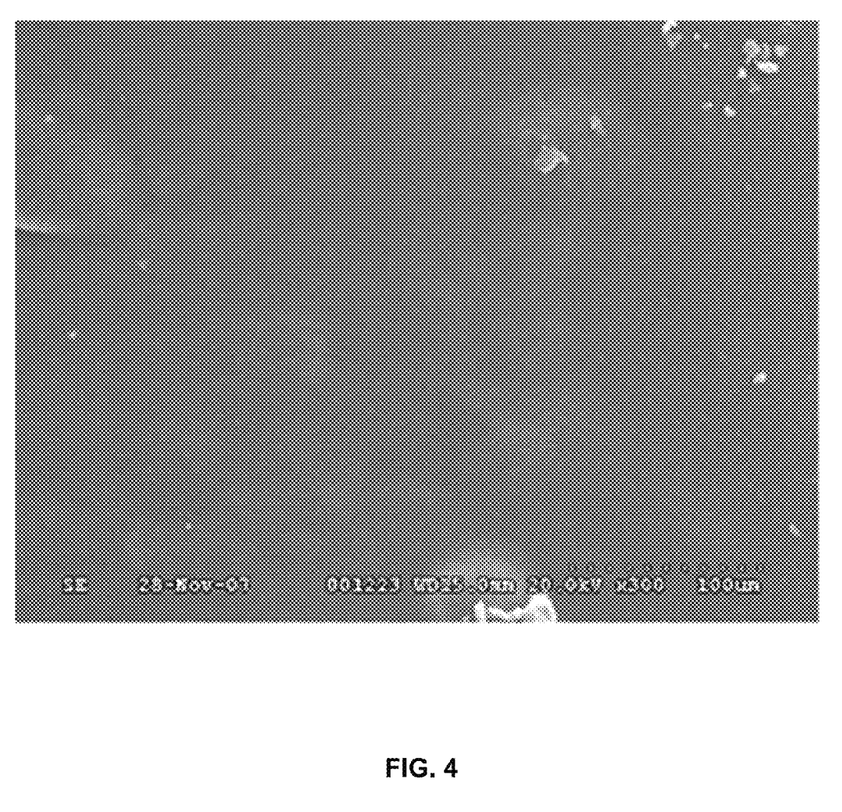
FIGS. 4 and 5 are SEM photographs showing a surface and a cross section of PDMT according to one exemplary embodiment of the present invention.
Figure 5:
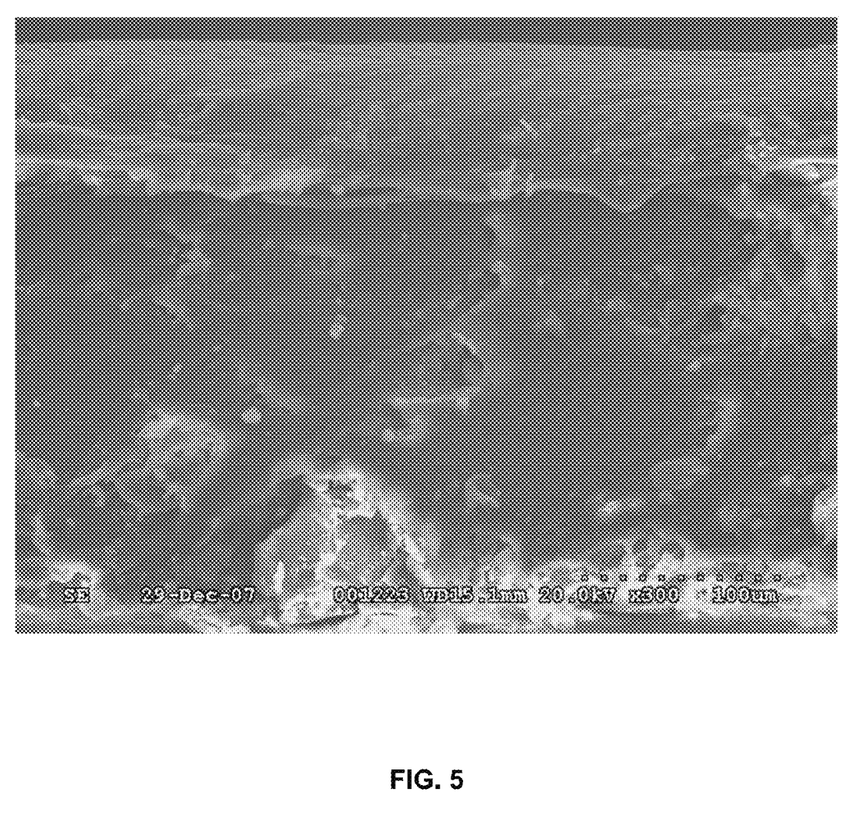

FIGS. 4 and 5 are SEM photographs showing a surface and a cross section of PDMT. Acetaminophen particles with a diameter of 20 μm or less were observed on the surfaces of the thermorods, and a mixed-drug layer and a coating layer were clearly observed in the photography of the cross section of PDMT.

Figure 6:
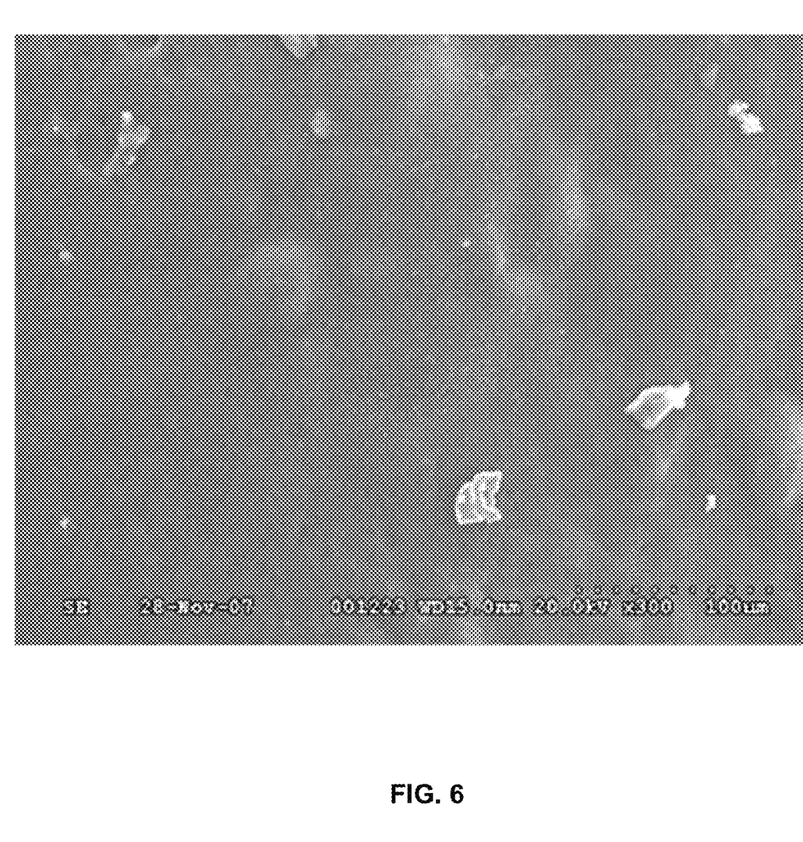
FIGS. 6 and 7 are SEM photographs showing a surface and a cross section of HPDMT according to one exemplary embodiment of the present invention.
Figure 7:
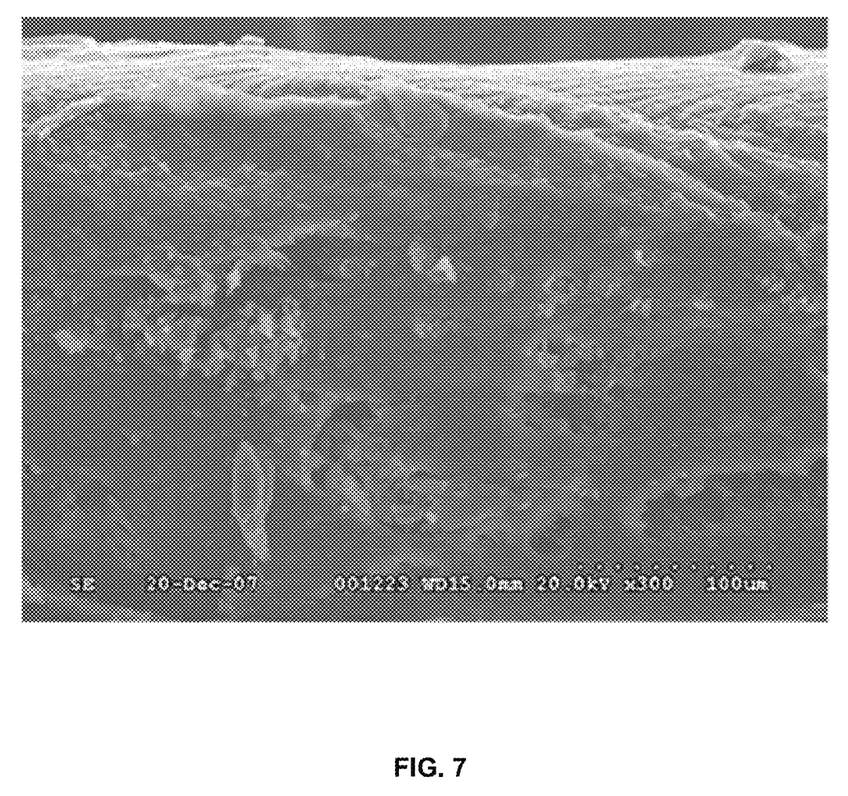

FIGS. 6 and 7 are SEM photographs showing a surface and a cross section of the HPDMT. Like PDMT, small acetaminophen particles were observed on the surfaces of the thermorods, and acetaminophen powder were also were observed in a cross section of the HPDMT.

Figure 8:
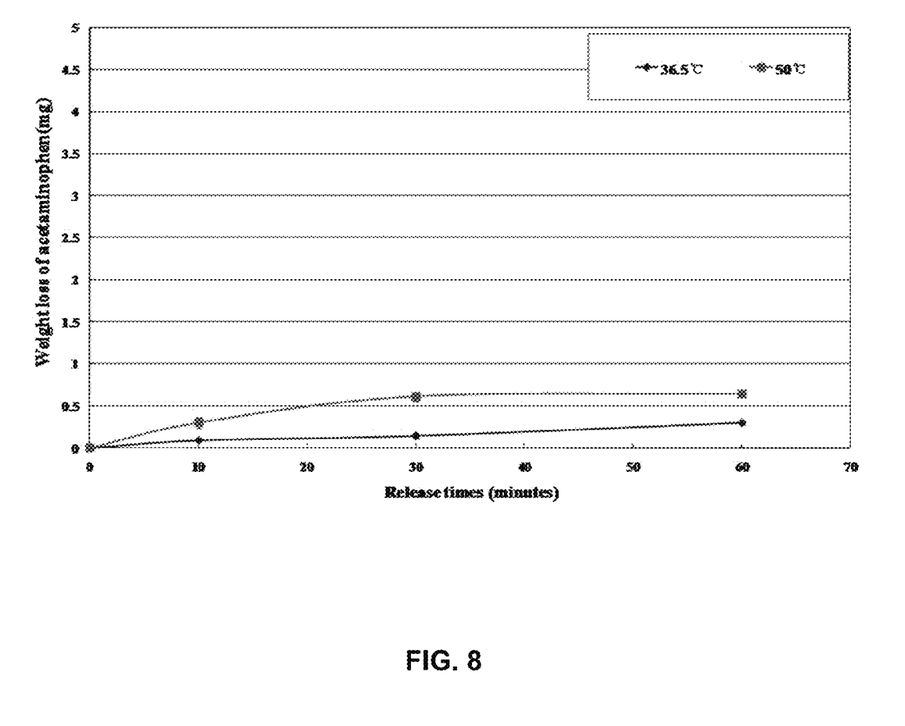
FIGS. 8 and 9 are diagrams showing data obtained by calculating the difference in weights of PDMT and HPDMT before and after their drug release according to one exemplary embodiment of the present invention.
Figure 9:
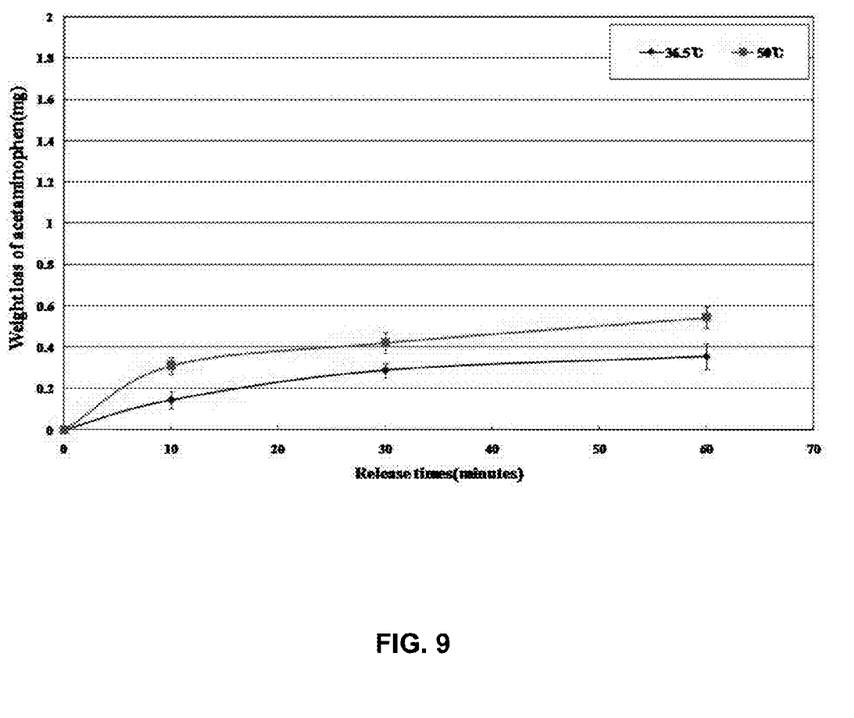

FIGS. 8 and 9 are diagrams showing data obtained by calculating the difference in weights of PDMT and HPDMT before and after drug release. The PDMT had an average drug release rate of 0.30 mg under the conditions of 60 minutes and 36.5° C., and an average drug release rate of 0.64 mg under the conditions of 60 minutes and 50° C. It was revealed thereby that PDMT has an average drug release rate at 50° C. that is 2 times higher than that at 36.5° C. The HPDMT had an average drug release rate at 36.5° C. of 0.36 mg and an average drug release rate at 50° C. of 0.54 mg. Then, it was revealed that the difference in the average drug release rate at both of the temperatures was 0.18 mg, which is half lower than the difference (0.34 mg) in average drug release rate of the PDMT at both of the temperatures. Therefore, it was seen that the drug release rate which varies according to changes in temperature varies according to the secondary dip-coating conditions.

Diffusion coefficients of the drugs obtained from the drug release tests were also compared, wherein it was revealed that the thermorods having a dip-coating layer formed therein have a lower diffusion coefficient than the thermorods with only a single mixed-drug layer that were not subject to the dip-coating process.

As described above, it was revealed that the thermorods comprising a mixed-drug layer may be used to effectively perform the drug administration since they may be used to perform the local hyperthermia at 36.5° C. or above and to actively control the active drug release delivery according to the coating conditions Although the preferred embodiments of the present invention have been disclosed for illustrative purposes, those skilled in the art will appreciate that various modifications, additions and substitutions are possible, without departing from the scope of the invention as disclosed in the accompanying claims.

What is claimed is:

1. A method for manufacturing a thermorod for active drug release that generates heat by means of eddy current loss and hysteresis loss in an induced magnetic field, comprising:
   processing the thermorod into a certain shape;
   preparing a mixed-drug specimen by mixing a drug with polyethylene-co-vinyl acetate as a support for the drug, which exhibits reduced capability to support the drug at an increased glass transition temperature;
   forming a mixed-drug layer on the surface of the thermorod by using the mixed-drug specimen; and
   forming a coating layer on a surface of the mixed-drug layer wherein the coating layer comprises polyethylene-co-vinyl acetate, poly(isobutylmethacrylate) or a mixture thereof.

2. The method according to claim 1, wherein the thermorod is made of at least one selected from the group consisting of iron, stainless steel, duplex stainless steel, nickel-copper alloy, iron-nickel alloy, palladium-cobalt alloy, iron-chromium alloy and iron-cobalt alloy.

3. The method according to claim 1, wherein the thermorod is processed into one shape selected from the group consisting of linear, platy, coiled or tubular shapes.

4. The method according to claim 1, wherein the coating layer is formed from a dip-coating solution prepared by dissolving polyethylene-co-vinyl acetate, poly (isobutylmethacrylate) or a mixture thereof in tetrahydrofuran.

5. A thermorod for active drug release that generates heat by means of eddy current loss and hysteresis loss in an induced magnetic field, comprising a mixed-drug layer formed by coating a surface of the thermorod with a mixed-drug specimen prepared by mixing a drug with polyethylene-co-vinyl acetate as a support for the drug, and a coating layer on a surface of the mixed-drug layer wherein the coating layer comprises polyethylene-co-vinyl acetate, poly(isobutylmethacrylate) or a mixture thereof.

6. The thermorod according to claim 5, wherein the thermorod is made of at least one selected from the group consisting of iron, stainless steel, duplex stainless steel, nickel-copper alloy, iron-nickel alloy, palladium-cobalt alloy, iron-chromium alloy and iron-cobalt alloy.

7. The thermorod according to claim 5, wherein the thermorod is processed into one shape selected from the group consisting of linear, platy, coiled or tubular shapes.

8. The thermorod according to claim 5, wherein the coating layer is formed from a dip-coating solution prepared by dissolving polyethylene-co-vinyl acetate, poly (isobutylmethacrylate) or a mixture thereof in tetrahydrofuran.

9. The thermorod according to claim 5, wherein the coating layer is formed on all surfaces of the mixed-drug layer.

\* \* \* \* \*